(12) United States Patent
Kagechika

(10) Patent No.: US 6,869,959 B1
(45) Date of Patent: Mar. 22, 2005

(54) HETEROCYCLIC CARBOXYLIC ACID DERIVATIVES

(75) Inventor: Hiroyuki Kagechika, Tokyo (JP)

(73) Assignee: Institute of Medicinal Molecular Design Inc., Tokyo (JP)

(*) Notice: Subject to any disclaimer, the term of this patent is extended or adjusted under 35 U.S.C. 154(b) by 0 days.

(21) Appl. No.: 09/926,407

(22) PCT Filed: Apr. 26, 2000

(86) PCT No.: PCT/JP00/02726

§ 371 (c)(1),
(2), (4) Date: Jan. 28, 2002

(87) PCT Pub. No.: WO00/66595

PCT Pub. Date: Nov. 9, 2000

(30) Foreign Application Priority Data

Apr. 28, 1999 (JP) .......................................... 11-121592

(51) Int. Cl.[7] ..................... A61K 31/505; C07D 239/42
(52) U.S. Cl. ...................................... 514/275; 544/332
(58) Field of Search .......................... 546/310; 544/407, 544/211, 224, 332, 329; 514/275

(56) References Cited

U.S. PATENT DOCUMENTS

| | | | |
|---|---|---|---|
| 3,415,834 A | 12/1968 | Hoffmann et al. | 260/295.5 |
| 3,466,373 A | 9/1969 | Hoffmann et al. | 424/266 |
| 3,499,898 A | 3/1970 | Van Beberburg | 260/256.4 |
| 4,143,151 A | 3/1979 | Wagner et al. | 424/279 |
| 4,207,330 A | 6/1980 | Wagner et al. | 424/275 |
| 4,666,915 A | 5/1987 | Ozeki et al. | 514/272 |
| 4,785,008 A | 11/1988 | Coquelet et al. | 514/342 |
| 4,788,195 A | 11/1988 | Torley et al. | 514/252 |
| 4,868,183 A | 9/1989 | Kanai et al. | 514/255 |
| 4,876,252 A | 10/1989 | Torley et al. | 514/224.8 |
| 5,059,598 A | 10/1991 | Kanai et al. | 514/247 |
| 5,672,710 A | 9/1997 | Beard et al. | 548/188 |
| 5,728,846 A | 3/1998 | Vuligonda et al. | 549/16 |
| 5,739,338 A | 4/1998 | Beard et al. | 546/153 |
| 5,760,276 A | 6/1998 | Beard et al. | 560/102 |
| 5,766,610 A | 6/1998 | Bernardon | 424/401 |
| 6,015,569 A | 1/2000 | Bernardon | 424/401 |
| 6,093,838 A | 7/2000 | Vasudevan et al. | 549/467 |
| 6,156,788 A | 12/2000 | Bernardon | 514/444 |
| 6,162,815 A | 12/2000 | Bernardon | 514/327 |

FOREIGN PATENT DOCUMENTS

| | | |
|---|---|---|
| EP | 493528 | 7/1970 |
| EP | 2926644 | 1/1980 |
| EP | 144730 | 6/1985 |
| EP | 254259 | 1/1988 |
| EP | 679630 | 11/1995 |
| JP | 61-22047 | 1/1986 |
| JP | 61-76440 | 4/1986 |
| JP | 6126-7580 | 11/1986 |
| JP | 62123180 | 4/1987 |
| JP | 1-131169 | 5/1989 |
| JP | 3-127790 | 5/1991 |
| JP | 03204813 | 6/1991 |
| JP | 9-100270 | 4/1997 |
| WO | 96/13478 | 5/1996 |
| WO | 97/02244 | 1/1997 |
| WO | 97/09297 | 3/1997 |
| WO | 97/11061 | 3/1997 |
| WO | 97/12853 | 4/1997 |
| WO | 97/34869 | 9/1997 |
| WO | 97/48672 | 12/1997 |
| WO | 98/45242 | 10/1998 |
| WO | 98/47854 | 10/1998 |
| WO | 99/33821 | 7/1999 |

OTHER PUBLICATIONS

English Language Abstract for JP 62 123180 A (Otsuka Pharmaceutical Factory Inc.), Jun. 4, 1987.
English Language Abstract for JP 03 204813 A (Otsuka Pharmaceutical Factory Inc.), Sep. 6, 1991.
K. Ozeki et al. "Studies on Antiallergy Agents. III" Chemical & Pharmaceutical Bulletin; vol. 37 (No. 7) pp. 1780–1787 (1989).
N. Finch et al. "Synthesis and Antihypertensive Activity of 5–amino–pyridinecarboxylic Acid Derivatives" Journal of Medicinal Chemistry; vol. 23 (No. 12) pp. 1405–1410 (1980).
Breaux et al., 18 J. Het. Chem. 183–84 (Jan. 1981).
Terashima et al., 43 (11) Chem. & Pharm. Bull. 2021–23 (Nov. 1995).
Gayo et al., 38 (2) Tett. Lett. 211–14 (Jan. 1997).
English Language Abstract of JP 61–22047, 1986.
English Language Abstract of JP 61–76440, 1986.
Journal of Medicinal Chemistry, 1988, vol. 31, No. 11, pp. 2182–2192.

(List continued on next page.)

Primary Examiner—Richard L. Raymond
(74) Attorney, Agent, or Firm—Greenblum & Bernstein, P.L.C.

(57) ABSTRACT

Compounds or salts thereof represented by the formula (I) wherein $R^1$ represents hydrogen atom, a $C_{1-6}$ alkyl group, a $C_{1-6}$ alkenyl group, or an acyl group, $R^2$ and $R^3$ represent hydrogen atom or a $C_{1-6}$ alkyl group, or adjacent $R^2$ and $R^3$ may combine to form 5- to 7-membered ring, $R^4$ represents hydrogen atom, hydroxyl group, a $C_{1-6}$ alkoxyl group, a $C_{1-6}$ alkyl group, HAr represents a heteroaryl-diyl group consisting of a 5-membered or 6-membered ring containing 1 to 3 hetero atoms, $R^5$ represents hydrogen atom or a $C_{1-6}$ alkyl group. The compounds or the salts thereof have retinoid-like physiological activities or controlling activity on physiological activities of retinoid.

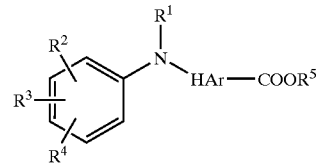

9 Claims, No Drawings

OTHER PUBLICATIONS

Evans, R. M., Science, 240, pp. 889–895, 1988.
Petkovich, M., et al., Nature, 330, pp. 444–450, 1987.
Hashimoto, Y., Cell Structure and Function, 16, pp. 113–123, 1991.
Hashimoto, Y., et al., Biochemical Biophysical Research Communications, vol. 166, pp. 1300–1307, 1990.
English Language Abstract of WO 97/11061, 1997.
English Language Abstract of WO 98/45242, 1998.
Mangelsdorf, D. J. et al., Nature, vol. 345, pp. 224–229, 1990.
Mangelsdorf, D. J. et al., The Retinoids, 2nd Edition, Raven Press, Ltd., pp. 319–349, 1994.
Eyrolles, L., et al., Journal of Medicinal Chemistry, 37(10), pp. 1508–1517, 1994.
English Language Abstract of JP 9–100270, 1997.
English Language Abstract of JP 61–267580, 1986.
English Language Abstract of JP 1–131169, 1989.
English Language Abstract of WO 97/34869, 1997.
English Language Abstarct of WO 97/09297, 1997.
English Language Abstract of WO 97/02244, 1997.
English Language Abstract of WO 96/13478, 1996.

HETEROCYCLIC CARBOXYLIC ACID DERIVATIVES

This application is a 371 of PCT/JP00/02726, filed Apr. 26, 2000.

TECHNICAL FIELD

The present invention relates to substances acting on retinoid receptors that have physiological activities similar to those of retinoids such as retinoic acid or controlling activities on retinoid actions, and medicaments comprising said compounds as active ingredients.

BACKGROUND ART

Retinoic acid (vitamin A acid), an active metabolite of vitamin A, has extremely important physiological functions inducing differentiation of immature cells under development processes toward mature cells having specific functions, enhancement of cell proliferation and life support action. It has been revealed that various vitamin A derivatives synthesized so far also have similar physiological functions, for example, the benzoic acid derivatives disclosed in Japanese Patent Unexamined Publication (KOKAI) Nos. (Sho)61-22047/1986 and (Sho)61-76440/1986, and the compounds described in Journal of Medicinal Chemistry, 1988, Vol. 31, No. 11, p.2182. "Retinoids" is a general term for retinoic acid and the aforementioned compounds having retinoic acid-like biological activities.

For example, it was proved that all-trans retinoic acid binds as a ligand to the retinoic acid receptor (RAR) present in cellular nucleus, which belongs to the intranuclear receptor super family (Evans, R. M., Science, 240, p.889, 1988), and regulates proliferation and differentiation of animal cells or cellular mortalities (Petkovich, M., et al., Nature, 330, pp.444–450, 1987). It has also been suggested that the aforementioned compounds having the retinoic acid-like biological activities, for example, 4-[(5,6,7,8-tetrahydro-5, 5,8,8-tetramethyl-2-naphthalenyl)carbamoyl]-benzoic acid: Am80, also bind to RAR in similar manners to retinoic acid to exhibit their physiological actions (see, Hashimoto, Y., Cell Struct. Funct., 16, pp.113–123, 1991; Hashimoto, Y., et al., Biochem. Biophys. Res. Commun., 166, pp.1300–1307, 1990).

Clinically, these compounds were found to be useful for therapeutic and preventive treatments of vitamin A deficiency disease, hyperkeratosis of epithelial tissue, rheumatism, delayed allergy, bone diseases, leukemia and certain types of cancer. However, due to the variety of biological activities of these retinoids, they are not fully satisfactory medicaments from a viewpoint of side effects. Therefore, it has been desired to create retinoids having characteristic activities and molecules controlling their activities.

As agents for controlling the activities of retinoids, benzodiazepine derivatives such as 4-[5H-2,3-(2,5-dimethyl-2, 5-hexano)-5-methyldibenzo[b,e](1,4]diazepin-11-yl] benzoic acid and 4-[1,3-dihydro-7,8-(2,5-dimethyl-2,5-hexano)-2-oxo-2H-1,4-benzodiazepin-5-yl] benzoic acid are known (PCT/JP96/2709, International Publication, WO97/11061). Furthermore, diphenylamine type compounds useful as agents for controlling the activities of retinoids are described on International Publication WO98/45242. Although these compounds, per se, have no retinoid action or their retinoid actions are feeble, they have remarkable enhancing actions on retinoids such as retinoic acid. Therefore, they have been suggested to be useful for therapeutic and preventive treatments of vitamin A deficiency disease, hyperkeratosis of epithelial tissue, rheumatism, delayed allergy, bone diseases, leukemia, and certain types of cancer.

As for expression of physiological activities of retinoic acid, existence of retinoid X receptor (RXR, of which ligand is 9-cis-retinoic acid) has been verified. It has been revealed that the retinoid X receptor forms a dimer with the retinoic acid receptor (RAR) to induce or suppress gene transcriptions, thereby controls the expression of the physiological activities of retinoic acid (Mangelsdorf, D. J. et al., Nature, 345, pp.224–229). It has also been revealed that the retinoid X receptor (RXR) binds to the intranuclear receptor of active vitamin $D_3$, PPAR whose involvement in lipid metabolism is suggested, and other receptors as well as to the retinoic acid receptor (RAR), thereby controls expression of actions of physiologically active substances binding to these receptors, for example, vitamin $D_3$, thyroxine and the like (Mangelsdorf, D. J. et al., The Retinoids, 2nd Ed., Raven Press, pp.319–350, 1994).

As agents for controlling retinoid actions, compounds are also known to exist which have antagonistic action against retinoids and attenuate typical actions of the above retinoids (Eyrolles, L., et al., Journal of Medicinal Chemistry, 37(10), pp.1508–1517, 1994). The above publication discloses that some compounds such as 4-(5H-7,8,9,10-tetrahydro-5,7,7, 10,10-pentamethylbenzo[e]naphtho[2,3-b][1,4]-diazepin-13-yl)benzoic acid act as retinoid antagonists. Moreover, certain compounds including 4-(13H-10,11,12,13-tetrahydro-10,10,13,13,15-pentamethylnaphtho[2,3-b]1-[1, 2-e][1,4]diazepin-7-yl)benzoic acid have been found as retinoid antagonists by the inventors of the present invention (specification of Japanese Patent Application No. (Hei)7-255912/1995).

DISCLOSURE OF THE INVENTION

An object of present invention is to provide substances acting on the retinoid receptor which have retinoid-like bioactivities or bioactivities of controlling the retinoid activities (for example, enhancing or suppressing activities on retinoid). Another object of the present invention is to provide medicaments which comprise said compound as active ingredients. Further object of the present invention is to provide, compounds useful as medicaments for preventive or therapeutic treatment of diabetes, and preventive or therapeutic treatment of complications of diabetes such as hyperlipidemia.

The inventors of the present invention conducted various studies to achieve the foregoing objects and found that compounds or salts thereof represented by the following general formula (I) have excellent retinoid-like bioactivities or controlling actions to retinoid bioactivities which are useful as active ingredients of medicaments, for example, those for preventive or therapeutic treatment of diabetes. The present invention was achieved on the basis of the above findings.

The present invention thus provides compounds represented by the following general formula (I)

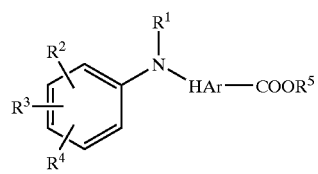

wherein $R^1$ represents hydrogen atom, a $C_{1-6}$ alkyl group, a $C_{1-6}$ alkenyl group, or an acyl group, $R^2$ and $R^3$ independently represent hydrogen atom or a $C_{1-6}$ alkyl group, or adjacent $R^2$ and $R^3$ groups may combine together with carbon atoms on the benzene ring to which they bind to form an aromatic 5- to 7-membered ring or non-aromatic 5-to 7-membered ring which may be substituted; $R^4$ represents hydrogen atom, hydroxyl group, a $C_{1-6}$ alkoxyl group, a $C_{1-6}$ alkyl group, nitro group, or a halogen atom; HAr represents a heteroaryl-diyl group consisting of a 5-membered or 6-membered ring which contains 1 to 3 hetero atoms and may be substituted; and $R^5$ represents hydrogen atom or a $C_{1-6}$ alkyl group.

The present invention also relates to a compound or a salt thereof represented by the following formula (I):

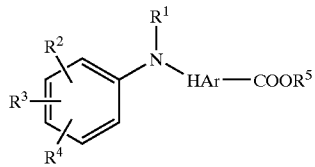

wherein $R^1$ represents hydrogen atom, a $C_{1-6}$ alkyl group, a $C_{1-6}$ alkenyl group, or an acyl group, $R^2$ and $R^3$ independently represent hydrogen atom or a $C_{1-6}$ alkyl group or adjacent $R^2$ and $R^3$ may combine together with carbon atoms on the benzene ring to which they bind to form an aromatic 5- to 7-membered ring or non-aromatic 5- to 7-membered ring which may be substituted; $R^4$ represents hydrogen atom, hydroxyl group, a $C_{1-6}$ alkoxyl group, a $C_{1-6}$ alkyl group, nitro group, or a halogen atom; and HAr—COOR$^5$ is 5-carboxy-pyrimidine-2-yl.

Moreover, the present invention also relates to medicament compositions of the compounds of the present invention, methods for treatment and/or prevention of diabetes, methods for treatment and/or prevention of complications of diabetes, and methods for controlling retinoid action.

According to another aspect of the present invention, medicaments comprising ski a substance, as an active ingredient, which is selected from group consisting of the compounds represented by the aforementioned general formula (I) or physiologically acceptable salts thereof, or hydrates thereof and solvates thereof are provided. These medicaments are useful as agents having retinoid-like actions or agents for controlling retinoid actions (preferably agents for enhancing retinoid activities or suppressing retinoid activities) or useful for preventive and/or therapeutic treatment of diabetes. According to further aspects of the present invention, use of the aforementioned substances for the manufacture of the aforementioned medicaments, and methods for therapeutic and/or preventive treatments of a disease in which a receptor belonging to the intranuclear receptor super family (Evans, R. M., Science, 240, p.889, 1988), preferably a retinoid receptor (RAR and/or RXR) is involved, which comprises the step of administering an effective amount of the aforementioned substances to a mammal including a human are provided.

BEST MODE TO CARRY OUT THE INVENTION $R^1$ represents hydrogen atom, a $C_{1-6}$ alkyl group, a $C_{1-6}$ alkenyl group, or an acyl group. In the specification, an alkyl group or an alkyl moiety of a functional group having the alkyl moiety (alkoxyl group, for example) may be linear, branched, cyclic or any combination thereof. Examples of the $C_{1-6}$ alkyl group represented by $R^1$ include, for example, methyl group, ethyl group, n-propyl group, isopropyl group, cyclopropylmethyl group, n-butyl group, sec-butyl group, tert-butyl group, cyclobutyl group, cyclobutylmethyl group, cyclopentyl group, and cyclohexyl group. As the alkyl group represented by $R^1$, cycloalkyl group or cycloalkylmethyl group is preferred, and cyclopropyl group or cyclopropylmethyl group is more preferred. As the $C_{1-6}$ alkenyl group represented by $R^1$, alkenyl group where 1 or 2, preferably 1 double bond is introduced to the aforementioned $C_{1-6}$ alkyl group may be used.

As the acyl group represented by $R^1$, alkylcarbonyl group, arylcarbonyl group, heterocyclic carbonyl group, arylalkylcarbonyl group, heterocyclic alkylcarbonyl group may be used. In the acyl group exemplified above, monocyclic or fused polycyclic aromatic groups may be used as an aryl moiety. For example, aromatic groups of 1 to 4 ring system, preferably monocyclic or bicyclic aromatic groups may be used. The number of carbon atoms of the aryl group may be 6 to 20, preferably 6 to 16, more preferably 6 to 12, and further preferably 6 to 10. More specifically, examples include phenyl group and naphthyl group.

In the acyl group exemplified above, monocyclic to 4 ring-system heterocyclic to; groups, preferably monocyclic to 3 ring-system heterocyclic groups, more preferably monocyclic or bicyclic heterocyclic groups, which contain one or more hetero atoms such as nitrogen atom, oxygen atom, and sulfur atom may be used as the hetero ring moiety. When 2 or more hetero atoms are contained, they may be the same or different. The hetero rings may be saturated, partially saturated, or aromatic ring. In the aforementioned acyl group, the hetero ring may bind in any position on the ring. As the hetero ring moiety of the aforementioned acyl group, for example, heteroaryl group such as pyridyl group, or saturated heterocyclic group such as piperazinyl group may be used. However, the hetero rings are not limited to these examples. Example: of the acyl group represented by $R^1$ include, for example, acetyl group, benzoyl group, benzyl carbonyl group, pyridyldimethylcarbonyl group.

The $C_{1-6}$ alkyl group or the acyl group represented by $R^1$ may be substituted. In the specification, when a functional group is referred to as "may be substituted", the functional group may optionally have one or more arbitrary substituents unless the substituent is not otherwise specified. When a functional group has 2 or more substituents, they may be the same or different. The positions of the substituents are not limited, and substituents may exist in any substitutable positions. The kinds of the substituents are not limited. Examples include, for example, alkyl group, alkenyl group, alkynyl group, aryl group, heterocyclic group, halogen atoms (a halogen atom referred to in the specification may be any one of fluorine atom, chlorine atom, bromine; atom, or iodine atom), hydroxyl group, oxo group, amino group, ammonium group, imino group, mercapto group, thioxo group, cyano group, nitro group, carboxyl group, phosphate group, sulfo group, hydrazino group, ureido group, imido group, isothiocyanate group, isocyanate group, alkoxy group, alkylthio group, aryloxy group, hetero cyclic oxy group, arylthio group, hetero cyclic thio group, aralkyl group, hetero cyclic alkyl group, aralkyloxy group, hetero cyclic alkyloxy group, alkoxycarbonyl group, aryloxycarbonyl group, hetero cyclic oxycarbonyl group, alkylcarbonyl group, arylcarbonyl group, hetero cyclic carbonyl group, alkylcarbonyloxy group, arylcarbonyloxy group, hetero cyclic carbonyloxy group, alkylcarbonylamino group, sulfonyl group, sulfinyl group, sulfonylamino group, carbamoyl group, or sulfamoyl.

Furthermore, the substituents exemplified above may be substituted by one or more other substituents. Examples of such groups include hydroxyalkyl group, haloalkyl group, mono or di-alkylamino group, haloalkylcarbonyl group, haloaryl group, hydroxyaryl group, mono or di-alkylcarbamoyl group. However, the above-explained substituents are given solely as examples, and substituents are not limited to these examples.

$R^2$ and $R^3$ independently represent hydrogen atom or a $C_{1-6}$ alkyl group. As the $C_{1-6}$ alkyl groups represented by $R^2$ and $R^3$, ethyl group or n-propyl group may be preferred, and bulky alkyl group such as isopropyl group, sec-butyl group, isobutyl group, tert-butyl group may also be preferred. When $R^2$ and $R^5$ both represent bulky alkyl groups, it is preferable that they substitute at positions on the benzene ring not adjacent to each other. When $R^2$ and $R^3$ are adjacent, $R^2$ and $R^3$ may combine together with the carbon atom on the phenyl ring to which they bind to form aromatic 5- to 7-membered ring or non-aromatic 5- to 7-membered ring. The ring thus formed may be substituted. Preferably, aromatic 6-membered ring or non-aromatic 6-membered ring may be formed.

For example, $R^2$ and $R^3$ may form saturated 5- or 6-membered ring together with 2 carbon atoms on the benzene ring to which each of them binds. The ring thus formed may be substituted with one or more $C_{1-4}$ alkyl group, for example, 2 to 4 methyl groups, preferably 4 methyl groups. For example, it is preferred that the benzene ring substituted with $R^2$ and $R^3$ together with $R^2$ and $R^3$ forms 5,6,7,8-tetrahydronaphthalene ring and 5,5,8,8-tetramethyl-5,6,7,8-tetrahydro-naphthalene ring. An aromatic 6-membered ring may be formed together with 2 carbon atoms on the benzene ring to which each of $R^2$ and $R^3$ binds. On the naphthalene ring thus formed, one or more substituents such as a $C_{1-6}$ alkyl group or a halogen atom may exist.

$R^4$ represents hydrogen atom, hydroxyl group, a $C_{1-6}$ alkoxyl group, a $C_{1-6}$ alkyl group, nitro group, or a halogen atom. As the $C_{1-6}$ alkoxyl group represented by $R^4$, for example, methoxy group, ethoxy group, n-propoxy group, isopropoxy group, n-butoxy group, sec-butoxy group, tert-butoxy group, preferably methoxy group may be used. As the $C_{1-6}$ alkyl group represented by $R^4$, for example, methyl group, ethyl group, n-propyl group, isopropyl group, n-butyl group, sec-butyl group, isobutyl group or tert-butyl group may be used. As the $C_{1-6}$ alkyl group represented by $R^5$, for example, methyl group, ethyl group, n-propyl group, isopropyl group, n-butyl group, sec-butyl group, isobutyl group, or tert-butyl group may be used.

Positions for substitution by $R^2$ and $R^5$ are not limited, and $R^2$ and $R^3$ may substitute at any position independently. However, when $R^2$ and $R^3$ form a ring, it is preferred that each of them is in para position and meta position relative to x, and when $R^2$ and $R^3$ do not form a ring, it is preferred that both of them are in meta position relative to X respectively. It is preferred that $R^4$ is in ortho position relative to X. The position of $R^4$ is not limited, and $R^4$ may substitute at any position on the benzene ting.

HAr represents a heteroaryl-diyl group consisting of a 5-membered or 6-membered ring which may contain 1 to 3 hetero atoms and may be substituted. The hetero aryl group contains 1 or more, preferably 1 to 3, more preferably 1 or 2 hetero atoms as ring constituent atoms, and may be a monocyclic ring or a fused ring system. When 2 or more hetero atoms are contained, they may be the same or different. As hetero atoms, for example, nitrogen atom, oxygen atom, sulfur atom may be used. Preferably, monocyclic hetero aryl-diyl groups may be used. More specifically, examples include, for example, pyridine-diyl group, pyrazine-diyl group, pyrimidine-diyl group, pyridazine-diyl group, triazine-diyl group, thiophene-diyl group, furan-diyl group, pyrrole-diyl group, imidazole-diyl group, pyrazole-diyl group, thiazole-diyl group, isothiazole-diyl group, oxazole-diyl group, isoxazole-diyl group. However, the heteroaryl-diyl groups are not limited to these examples. Preferably, pyrimidine-diyl group may be used. Positions for bonding of heteroaryl-diyl group are not limited, however, it is preferred that the carboxyl group is in meta or para position relative to X.

The compounds of the present invention may occasionally exist in the form of salts such as acid addition salts or base addition salts. Examples of the acid addition salts include mineral acid salts such as hydrochloride or hydrobromide, or organic acid salts such as p-toluene sulfonate, methane sulfonate, oxalate or tartrate. Base addition salts are formed when $R^5$ represents hydrogen atom. As the base addition salts, metal salts such as sodium salt, potassium salt, magnesium salt or calcium salt, and organic amine salts such as ammonium salt, triethyl amine salt or ethanol amine salt may be used. The compound may also form amino acid salts such as glycine salt.

The compound of the present invention represented by the formula (I) may have one or more asymmetric carbon atoms depending on the kind of substituents. Any optical isomers, any mixtures of optical isomers, and racemate based on these asymmetric carbons, diastereo isomers and any mixtures of diastereo isomers based on 2 or more asymmetric carbons are all encompassed within the scope of the present invention. The compounds which have one or more double bonds may be geometrical isomers in a pure form or mixtures of geometrical isomers. Any hydrates or solvates of the compounds in free form or in the form of a salt also fall within the scope of the present invention.

Preferred examples of the compounds of the present invention represented by the formula (I) are shown below. However, the compounds of the present invention are not limited to these examples.

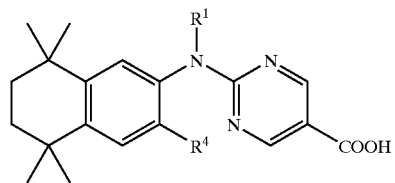

| | $R^1$ | $R^4$ |
|---|---|---|
| 1 | H | H |
| 2 | $CH_3$ | H |
| 3 | $n-C_3H_7$ | H |
| 4 | $CH_2-cC_3H_5$ | H |
| 5 | H | $CH_3$ |
| 6 | $CH_3$ | $CH_3$ |
| 7 | $n-C_3H_7$ | $CH_3$ |
| 8 | $CH_2-cC_3H_5$ | $CH_3$ |

-continued

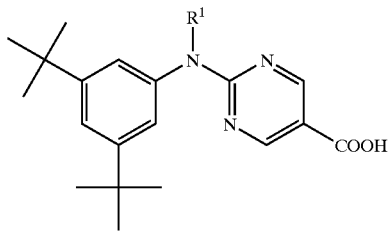

9  CH₃
10 C₂H₅
11 n-C₃H₇
12 CH₂-c-C₃H₅

As for the preparation of the compounds of the aforementioned formula (I), synthetic examples of the aforementioned typical compounds are specifically detailed in the examples given in the specification. Therefore, those skilled in the art will be able to readily prepare any compounds falling within the compounds of the present invention represented by the aforementioned formula (I) by referring to those examples, or if necessary, appropriately altering or modifying the disclosed methods.

The compounds of the aforementioned formula (I) can interact with a retinoid receptor (the term "retinoid receptor" used in the specification encompasses the retinoic acid receptors RAR and RXR, and the term means one or more of receptors with which a retinoid such as all-trans-retinoic acid and 9-cis-retinoic acid can interact), and they, per se, exhibit a retinoid-like physiological activities as an agonist, or have an action for enhancing or suppressing the physiological activities of retinoids. Preferably, they can enhance physiological activities of retinoids.

Therefore, the medicaments comprising the aforementioned compound as an active ingredient are useful as agents having retinoid-like activities or agents for controlling retinoid activities. Which of the actions the compound of the aforementioned formula (I) possesses can be easily determined by a method described in detail in the examples of the specification or methods described the literature. A method for evaluation of compounds enhancing retinoid activities is described in International Publication WO97/11061 (PCT/JP96/2709), and an evaluation for compounds suppressing retinoid activities is described in Eyrolles, L., et al., Journal of Medicinal Chemistry, 37 (10), pp.1508–1517, 1994, and in the specification of Japanese Patent Application No. (Hei)7-255912/1995.

Among the aforementioned compounds, those exhibiting retinoid-like activities have, for example, cell differentiation activity, cell proliferation enhancing activity, life supporting activity, and they can be used as active ingredients of medicaments for preventive or therapeutic treatments of vitamin A deficiency disease, hyperkeratosis of epithelial tissue, psoriasis, allergic diseases, immunological diseases such as rheumatism, bone diseases, leukemia, or cancers. Among the aforementioned compounds, those enhancing retinoid activities, per se, have substantially no retinoid-like activity, or they have slight or moderate retinoid-like activities. However, when those compounds are allowed to coexist with a retinoid such as retinoic acid, the physiological activities of the retinoid (typical examples include cell differentiation activity, cell proliferation enhancing activity, life supporting activity) are remarkably enhanced.

Although it is not intended to be bound by any specific theory, where the compound enhancing retinoid activities, per se, exhibits retinoid activities, synergistic actions are achieved. Therefore, where retinoids such as retinoic acid or the aforementioned compounds having retinoic acid-like biological activities (for example, 4-[(5,6,7,8-tetrahydro-5,5,8,8-tetramethyl-2-naphthalenyl)carbamoyl] benzoic acid: Am80) are administered) as medicaments for the preventive or therapeutic treatments of vitamin A deficiency disease, hyperkeratosis of epithelial tissue, psoriasis, allergic diseases, immunological diseases such as rheumatism, bone diseases, leukemia, or cancers, the compounds enhancing retinoid activities can be used as agents that enhance the activities of the retinoids.

Even when retinoids are not administered for the preventive and therapeutic treatments of the aforementioned diseases, the compounds enhancing retinoid activities can increase the activities of retinoic acid that inherently exists in living bodies, and thus the compounds may be administered as medicaments for the purpose of the preventive and therapeutic treatments of the aforementioned diseases. Furthermore, the aforementioned compounds may be used, in addition to the enhancement of the activities of retinoids, to enhance activities of physiologically active substances such as steroid compounds, vitamin D compounds including vitamin $D_3$, or thyroxine which bind to receptors belonging to the intranuclear receptor super family present in cellular nucleus to exhibit their physiological activities (Evans, R. M., Science, 240, p.889, 1988). They are useful as medicaments for preventive or therapeutic treatments of, for example, diabetes, arteriosclerosis, hyperlipidemia, hypercholesterolemia, bone diseases, rheumatism, immunological diseases.

As the intranuclear receptors, for example, the intranuclear receptor for active vitamin $D_3$, the PPAR involved in lipid metabolism, the thyroxine receptor, the COUP are known (for these receptors, see, Mangelsdorf, D. J. et al., The Retinoids, 2nd Ed., Raven Press, pp.319–350, 1994). It has been revealed that these receptors bind to the; retinoid X receptor (RXR) to have the aforementioned physiologically active substances exhibit their activities.

Among the aforementioned compounds, those suppressing retinoid activities have an action of markedly suppressing the physiological activities of retinoids (typical examples include cell differentiation activity, cell proliferation enhancing activity, life supporting activity and the like). Although it is not intended to be bound by any specific theory, it is believed that compounds having such an action bind to retinoid X receptor (RXR), which forms a dimer with the retinoic acid receptor (RAR), thereby control the expression of the physiological activity of retinoids such as retinoic acid. These compounds are useful for preventive and/or therapeutic treatments of endogenous hypervitaminosis of vitamin A caused by excessive vitamin A in vivo, or exogenous hypervitaminosis of vitamin A caused by retinoic acid or a compound having retinoic acid-like biological activities (for example, 4-[(5,6,7,8-tetrahydro-5,5,8,8-tetramethyl-2-naphthalenyl)carbamoyl] benzoic acid: Am80 or the like) which is administered for therapeutic or preventive treatment of vitamin A deficiency disease, hyperkeratosis of epithelial tissue, psoriasis, allergic diseases, immunological diseases such as rheumatism, bone diseases, leukemia, or cancers.

Cancers such as leukemia can be treated by administering the compounds suppressing retinoid activities, per se, alone or in combination with other retinoid or an antitumor agent. The aforementioned compounds can suppress activities of substances that bind to a receptor belonging to the intranuclear receptor super family present in the nucleus of cells (Evans, R. M., Science, 240, p.889, 1988) to express physiological activities, for example, steroid compounds, vitamin D compounds such as vitamin $D_3$, thyroxine and orphan receptors whose ligands are unknown. Accordingly, the aforementioned compounds can also be used for controlling the expression of the physiological activities of these substances. The compounds suppressing retinoid activities which bind to the retinoid X receptor (RXR) can be thus used, for example, preventive and/or therapeutic treatments of diseases with abnormalities of biological activities in which one or more of receptors belonging to the intranuclear receptor super family are involved.

According to the most preferred embodiment of the present invention, the medicaments of the present invention may be used for the preventive and/or the therapeutic treatments of diabetes. The cause and morbid state of treatable diabetes are not limited. For example, both of insulin dependent diabetes mellitus (IDDM) and non-insulin dependent diabetes mellitus (NIDDM) are applicable targets. Those based on the abnormality of insulin reactions (for example, disorders of use of intracellular glucose, insulin receptor functional disorders, structural abnormality of insulin, those related to administration of glucocorticoid); those based on insulin secretion abnormality (abnormality of signal transmission such as mutation of glucokinase gene, partial destruction of pancrease β cell by pancreatitis and automune mechanism); those by nutrition lesion are all applicable targets of the medicaments of the present invention.

Generally, treatments of diabetes are conducted for the purpose of prevention of the onset of acute and chronic complications or suppression of progression thereof. The medicaments of the present invention may be used for the purpose of preventive and/or therapeutic treatments of the complication of diabetes. The term "preventive treatments" used in the specification should be construed in the broadest sense including the prevention of the onset of diabetes or its complications. Furthermore, the term "therapeutic treatment" used in the specification should be construed in the broadest sense including the fundamental cure of the disease or its complications, remission of symptoms, suppression of progression of morbid state. Examples of the complications of diabetes which are suitable applicable targets of the medicaments of the present invention include, for example, retinopathy, nephrosis, neuropathy, hyperlipidemia. Among them, hyperlipidemia resulting from diabetes is a suitable applicable target of the medicaments of the present invention.

When the medicaments of the present invention are used for the preventive and/or therapeutic treatments of diabetes, or preventive and/or therapeutic treatments of complications of diabetes, they may be used together with other medicaments used for the same purposes. For example, when thiazoline compounds used for the treatment of diabetes or agents having insulin action are used together with the medicaments of the present invention, actions of the medicaments of the present invention may sometimes be enhanced synergistically. Accordingly, combined uses with the above medicaments are preferred embodiments of the medicaments of the present invention. Examples of the thiazoline compounds used for the treatment of diabetes include, for example, troglitazone "Noscal" Sankyo), pioglitazone (disclosed in Japanese Patent Unexamined Publication (KOKAI) No. (Sho) 61-267580/1986), BRL49652 (disclosed in Japanese Patent Unexamined Publication (KOKAI) No. (Hei) 1-131169/1989). Examples of the agents having insulin action include insulin, insulin secretion promoting agents (glipemide·Hoechst Marion Roussel Co., Ltd.). In addition, medicaments such as sulfone urea agents, biguanide-type hypoglycemic agents or α-glucosidase inhibitor may be used in combination.

As the medicament of the present invention, the aforementioned substance, per se, may be administered. However, a pharmaceutical composition for oral administration or parenteral administration may preferably be administered which can be prepared by a method well known to those skilled in the art. Examples of the pharmaceutical compositions suitable for oral administrations include, for example, tablets, capsules, powders, subtilized granules, granules, liquids, and syrups. Examples of the pharmaceutical compositions suitable for parenteral administrations include, for example, injections, suppositories, inhalants, eye drops, nasal drops, ointments, creams, and patches. The aforementioned pharmaceutical compositions may be prepared by the addition of pharmacologically and pharmaceutically acceptable additives. Examples of pharmacologically and pharmaceutically acceptable additives include, for example, excipients, disintegrators and disintegrating aids, binders, lubricants, coating agents, colorants, diluents, base materials, dissolving agents and dissolving aids, isotonic agents, pH modifiers, stabilizers, propellants, and adhesives.

The doses of the medicaments of the present invention are not particularly limited, and appropriate doses are easily selected in various administration methods. For example, for oral administration, the medicament may be used in a dose of 0.01 to 1,000 mg per day for an adult. However, it is desirable that the dose may be suitably increased or decreased depending on the age and body weight of a patient, the presence of complications or symptoms, purpose of treatment or prevention and the like. Also, when medicaments comprising a thiazoline compound or an agent having insulin action as an active ingredient and the medicament of the present invention are used in combination, it is possible to administer the medicament of the present invention during the administration period of the medicaments comprising a thiazoline compound or an agent having insulin action as an active ingredient, and/or in any period before or after said period.

EXAMPLES

The present invention will be more specifically explained by examples. However, the scope of the present invention is not limited to the scope of these examples below. Compound numbers in the examples correspond to the compound numbers of the compounds described as preferred compounds above.

Example 1

Preparation of 2-[N-(5,6,7,8-Tetrahydro-5,5,8,8-tetramethylnaphthalen-2-yl)amino]pyrimidine-5-carboxylic Acid (Compound 1)

A mixture of ethyl 2-chloropyrimidine-6-carboxylate (100 mg), 5,6,7,8-tetrahydro-5,5,8,8-tetramethylnaphthalen-2-amine (108 mg), and $K_2CO_8$ (400 mg) was heated at 110° C. After the disappearance of the materials was observed with TLC, the reaction mixture was poured into water, and extracted with $CH_2Cl_2$. The organic layer was dried over $Na_2SO_4$, and the solvent was evaporated. The residue was purified by silica gel flash column chromatography (n-hexane: AcOEt=20:1) to give white crystals of ethyl 2-[N-(5,6,7,8-tetrahydro-5,5,8,8-tetramethyl-naphthalen-2-yl)amino]pyrimidine5-carboxylate (170 mg, 91%).

Colorless Cottons (n-hexane-AcOEt);

$^1$H-NMR (400 MHx, CDCl$_3$) δ 8.95 (s, 2H), 7.56 (br s, 1H), 7.44 (dd, J=2.4, 9.0 Hz, 1 H), 7.44 (d, J=2.4 Hz, 1H), 7.31 (d, J=9.2 Hz, 1H), 4.37 (q, J=7.0 Hz, 2 H), 1.69 (s, 4 H), 1.39 (t, J=7.1 Hz, 3H), 1.30 (s, 6H), 1.28 (s, 6H).

Ethyl 2-[N-(5,6,7,8-tetrahydro-5,5,8,8-tetramethylnaphthalen-2-yl)amino]-pyrimidine-5-carboxylate (52 mg) was dissolved in ethanol (3 ml), and the solution was added with a 20% aqueous solution of KOH (0.5 ml) and heated at reflux. After the disappearance of the materials was observed with TLC, the reaction mixture was poured into 2N hydrochloric acid, and extracted with Ethyl acetate. The organic layer was dried over Na$_2$SO$_4$, and the solvent was evaporated to give white crude crystals of compound 1 (52 mg, quant).

Compound 1:

Colorless Prisms (n-hexane-AcOEt); mp>300° C.;

$^1$H-NMR (400 MHz, CDCl$_3$) δ 9.94 (s, 1H), 8.83 (s, 2H), 7.57 (s, 1H), 7.55 (d, J=4.5 Hz, 1 H), 7.26 (d, J=8.4 Hz, 1 H), 1.65 (s, 4 H), 1.25 (s, 6H), 1.24 (s, 6H); Anal. Calcd for C$_{19}$H$_{23}$N$_3$O$_2$.½H$_2$O, C: 68.24%, H: 7.23%, N: 12.57%; Found C: 68.51%, H: 7.02%, N: 12.59%.

Example 2

Preparation of 2-[N-Methyl-N-(5,6,7,8-tetrahydro-5,5,8,8-tetramethyl-naphthalen-2-yl)amino]pyrimidine-5-carboxylic Acid (Compound 2)

Ethyl 2-[N-(5,6,7,8-tetrahydro-5,5,8,8-tetramethylnaphthalen-2-yl)amino]-pyrimidine-5-carboxylate (104 mg) was dissolved in dry DMF (3 ml), and the solution was added with a suspension of NaH (40 mg) in DMF (2 ml). The mixture was then added with methyl iodide (0.5 ml) and stirred. After the disappearance of the materials was observed with TLC, the reaction mixture was poured into water, and extracted with CH$_2$Cl$_2$. The organic layer was dried over Na$_2$SO$_4$, and the solvent was evaporated. The residue was purified by silica gel flash column chromatography (n-hexane: AcOEt=20:1) to obtain white crystals of ethyl 2-[N-methyl-N-(5,6,7,8-tetrahydro-5,5,8,8-tetramethylnaphthalene-2-yl)amino]pyrimidine-5-carboxylate (105 mg, 97%).

$^2$H-NMR (400 MHz, CDCl$_3$) δ 8.88 (s, 2 H), 7.33 (d, J=8.4 Hz, 1 H), 7.20 (d, J=2.2 Hz, 1 H), 7.06 (dd, J=2.2, 8.2 Hz, 1H), 4.34 (q, J=7.1 Hz, 2 H), 3.57 (s, 3 H), 1.70 (s, 4 H), 1.36 (t, J=7.1 Hz, 3 H), 1.30 (s, 6H), 1.28 (s, 6 H).

Ethyl 2-[N-methyl-N-(5,6,7,8-tetrahydro-5,5,8,8-tetramethylnaphthalene-2-yl)amino]pyrimidine-5-carboxylate (75 mg) was dissolved in ethanol (4 ml), and the solution was added with a 20% aqueous solution of KOH (0.5 ml) and heated at reflux. After the disappearance of the materials was observed with TLC, the reaction mixture was poured into 2 N hydrochloric acid, and extracted with Ethyl acetate. The organic layer was dried over Na$_2$SO$_4$, and the solvent was evaporated to give white crude crystals of compound 2 (70 mg, quant).

Compound 2:

Colorless Needles (EtOH); mp>300° C.;

$^1$H-NMR (400 MHz, DMSO-d$_6$) δ 8.75 (s, 2H), 7.34 (d, J=8.4 Hz, 1 H), 7.26 (d, J=2.2 Hz, 1 H), 7.07 (dd, J=2.2, 8.2 Hz, 1 H), 3.49 (s, 3 H), 1.67 (8, 4 H), 1.27 (s, 6 H), 1.24 (s, 6 H);

Anal. Calcd for C$_{20}$H$_{25}$N$_3$O$_2$, C: 70.77%, H: 7.42%, N: 12.38%; Found C: 70.49%, H: 7.43%, N: 12.26%.

Example 3

Preparation, of 2-[N-n-Propyl-N5,6,7,8-tetrahydro-5,5,8,8-tetramethyl-naphthalen-2-yl)amino]pyrimidine-5-carboxylic Acid (Compound 3)

Ethyl 2-[N-(5,6,7,8-tetrahydro-5,5,8,8-tetramethylnaphthalene-2-yl)amino]-pyrimidine-5-carboxylate (165 mg) was dissolved in dry DMF (3 ml), and the solution was added with a suspension of NaH (130 mg) in DMF (2 ml). Then, the mixture was added with n-propyl iodide (0.5 ml) and stirred. After the disappearance of the materials was observed with TLC, the reaction mixture was poured into water, and extracted with CH$_2$Cl$_2$. The organic layer was dried over Na$_2$SO$_4$, and the solvent was evaporated. The residue was purified by silica gel flash column chromatography (n-hexane: AcOEt=20:1) to obtain ethyl 2-[N-n-propyl-N-(5,6,7,8-tetrahydro-5,5,8,8-tetramethylnaphthalene-2-yl)amino]pyrimidine-5-carboxylate (116.5 mg, 63%).

Ethyl 2-[N-n-propyl-N-(5,6,7,8-tetrahydro-5,5,8,8-tetramethylnaphthalene-2-yl)amino]pyrimidine-5-carboxylate (116.5 mg) was dissolved in ethanol (5 ml), and the solution was added with a 20% aqueous solution of KOH (1 ml) and heated at reflux. After the disappearance of the materials was observed with TLC, the reaction mixture was poured into 2 N hydrochloric acid, and extracted with Ethyl acetate. The organic layer was dried over Na$_2$SO$_4$, and evaporated to give white crude crystals of compound 3 (108 mg, quant).

Compound 3:

Colorless Prisms (n-hexane-AcOEt); mp 222° C.;

$^1$H-NMR (400 MHz, CDCl$_3$) δ 8.8 (s, 2 H), 7.43 (d, J=8.5 Hz, 1H), 7.26 (d, J=2.3 Hz, 1H), 7.08 (dd, J=2.3, 8.5 Hz, 1 H), 3.99 (t, J=7.8 Hz, 2H), 1.74 (s, 4 H), 1.66 (6 th, J=7.1 Hz, 2 H), 1.35 (s, 6 H), 1.31 (s, 6H), 0.93 (t, J=7.3 Hz, 3 H);

Anal. Calcd for C$_{22}$H$_{29}$N$_3$O$_2$, C: 71.90%, H: 7.95%, N: 11.44%; Found C: 71.79%, H: 7.99%, N: 11.25%.

Example 4

Preparation of 2-[N-Cyclopropylmethyl-N-(5,6,7,8-tetrahydro-5,5,8,8-tetramethylnaphthalen-2-yl)amino]pyrimidine-5-carboxylic Acid (Compound 4)

Ethyl 2-[N-(6,6,7,8-tetrahydro-5,5,8,8-tetramethylnaphthalen-2-yl)amino]-pyrimidine-5-carboxylate (100 mg) was dissolved in dry DMF (2 ml), and the solution was added with a suspension of NaH (30 mg) in DMF (1.5 ml), and then the mixture was added with cyclopropylmethyl bromide (0.3 ml) and stirred. After the disappearance of the materials was observed with TLC, the reaction mixture was poured into water, and extracted with CH$_2$Cl$_2$. The organic layer was dried over Na$_2$SO$_4$, and the solvent was evaporated. The residue was purified by silica gel flash column chromatography (n-hexane AcOEt=20:1) to obtain ethyl 2-[N-cyclopropyl-methyl-N -(5,6,7,8-tetrahydro-5,5,8,8-tetramethylnaphthalene-2-yl)amino]pyrimidine-5-carboxylate (63 mg, 55%).

$^3$H-NMR (400 MHz, CDCl$_3$) δ 8.85 (s, 2 H), 7.33 (d, J=8.4 Hz, 1 H), 7.18 (d, J=2.2 Hz, 1 H), 7.01 (dd, J=2.2, 8.3 Hz, 1 H), 4.33 (q, J=7.2 Hz, 2 H), 3.86 (d, J=7.0 Hz, 2 H), 1.70 (s, 4 H), 1.35 (t, J=7.0 Hz, 3 H), 1.30 (s, 6 H). 1.27 (s, 6 H), 1.17 (br m, 1 H), 0.46 (dd, J=5.9, 12.6 Hz, 2 H), 0.19 (dd, J=5.0, 10 Hz, 2 H).

Ethyl 2-[N-cyclopropylmethyl-N5,6,7,8-tetrahydro-5,5,8,8-tetramethyl-naphthalen-2-yl)amino]pyrimidine-5-carboxylate (63 mg) was dissolved in ethanol (4 ml), and the solution was added with a 20% aqueous solution of KOH (0.5 ml) and heated at reflux. After the disappearance of the materials was observed with TLC, the reaction mixture was poured into 2 N hydrochloric acid, and extracted with ethyl acetate. The organic layer was dried over $Na_2SO_4$, and the solvent was evaporated to give white crude crystals of compound 4 (55 mg, 85.5%).

Compound 4:
Colorless Needles (n-hexane-AcOEt); mp 232° C.;
$^1$H-NMR (400 MHz, DMSO-$d_6$) δ 8.73 (s, 2 H), 7.36 (d, J=8.4 Hz, 1 H), 7.22 (d, J=1.2 Hz, 1 H), 7.02 (dd, J=1.2, 8.4 Hz, 1 H), 3.84 (d, J=6.8 Hz, 2 H), 1.67 (s, 4 H), 1.28 (s, 6 H), 1.24 (s, 6 H), 1.18 (br m, 1 H), 0.42 (dd, J=5.1, 13 Hz, 2 H), 0.14 (dd, J=5.1, 10 Hz, 2 H);
Anal. Calcd for $C_{23}H_2N_3O_2 \cdot 1/10 H_2O$, C: 72.64%, H: 7.47%, N: 11.05%; Found C: 72.35%, H: 7.67%, N: 10.81%.

Example 5

Preparation of 2-[N-(5,6,7,8-Tetrahydro-3,5,5,8,8-pentamethyl naphthalen-2-yl)amino]pyrimidine-5-carboxylic Acid (Compound 5)

A mixture of ethyl 2-chloropyrimidine-5-carboxylate (424 mg), 5,6,7,8-tetrahydro-3,5,5,8,8-pentamethylnaphthalen-2-amine (497 mg), and $K_2CO_3$ (1.0 g) was heated at 110° C. After the disappearance of the materials was observed with TLC, the reaction mixture was poured into water, and extracted with $CH_2Cl_2$. The organic layer was dried over $Na_2SO_4$, and the solvent was evaporated. The residue was purified by silica gel flash column chromatography (n-hexane: AcOEt=10:1) to give pale yellow crystals of ethyl 2-[N-(5,6,7,8-tetrahydro-3,5,5,8,8-pentamethyl-naphthalen-2-yl)amino] pyrimidine-5-carboxylate (506 mg, 61%).

Colorless Prisms (n-hexane-AcOEt);
$^1$H-NMR (400 MHz, CDCl$_3$) δ 8.93 (s, 2 H), 7.69 (s, 1 H), 7.16 (s, 1 H), 4.37 (q, J=7.1 Hz, 2 H), 2.26 (s, 3 H), 1.69 (s, 4 H), 1.39 (t, J=7.1 Hz, 3 H), 1.29 (s, 6 H), 1.28 (s, 6 H).

Ethyl 2-[N-(5,6,7,8-tetrahydro-3,5,5,8,8-pentamethylnaphthalene-2-yl)amino]-pyrimidine-5-carboxylate (53 mg) was dissolved in ethanol (2 ml), the solution was added with a 20% aqueous solution of KOH (0.5 ml) and heated at reflux. After the disappearance of the materials was observed with TLC, the reaction mixture was poured into 2 N hydrochloric acid, and extracted with ethyl acetate. The organic layer was dried over $Na_2SO_4$, and the solvent was evaporated to give white crude crystals of compound 5 (49 mg, quant).

Compound 5:
Colorless Needles (n-hexane-AcOEt); mp 267° C.;
$^1$H-NMR (400 MHz, DMSO-$d_6$) δ 9.39 (s, 1 H), 8.73 (s, 2 H), 7.20 (s, 1 H), 7.16 (s, 1 H), 2.10 (s, 3 H), 1.64 (s, 4 H), 1.25 (s, 6 H), 1.21 (s, 6 H); Anal. Calcd for $C_{20}H_{25}N_3O_2$, C: 70.77%, H: 7.42%, N: 12.38%; Found C: 70.49%, H: 7.42%, N: 12.27%.

Example 6

Preparation of 2-[N-Methyl-N-(5,6,7,8-tetrahydro-3,5,5,8,8-pentamethyl-naphthalen-2-yl)amino]pyrimidine-5-carboxylic Acid (Compound 6)

Ethyl 2-[N-(5,6,7,8-tetrahydro-3,5,5,8,8-pentamethylnaphthalene-2-yl)amino]-pyrimidine-5-carboxylate (80 mg) was dissolved in dry DMF (2 ml), and the solution was added with a suspension of NaH (34 mg) in DMF (1 ml). The mixture was then added with methyl iodide (0.5 ml) and stirred. After the disappearance of the materials was observed with TLC, the reaction mixture was poured into water, and extracted with $CH_2Cl_2$. The organic layer was dried over $Na_2SO_4$, and the solvent was evaporated. The residue was purified by silica gel flash column chromatography (n-hexane: AcOEt=10:1) to obtain white crystals of ethyl 2-[N-methyl-N-5,6,7,8-tetrahydro-3,5,6,8,8-pentamethylnaphthalen-2-ylamino)pyrimidine-5-carboxylate (80 mg, 96%).

$^1$H-NMR (400 MHz, CDCl$_3$) δ 8.96 (a, 1 H), 8.80 (s, 1 H), 7.19 (s, 1 H), 7.05 (s, 1 H), 4.33 (q, J=7.2 Hz, 2 H), 3.47 (a, 3 H), 2.06 (s, 3 H), 1.68 (s, 2 H), 1.68 (B, 2 H), 1.35 (t, J=7.2 Hz, 3 H), 1.32 (s, 3 H), 1.28 (s, 3 H), 1.26 (s, 3 H), 1.25 (s, 3 H).

Ethyl 2-[N-methyl-N-(5,6,7,8-tetrahydro-3,5,5,8,8-pentamethylnaphthalen-2-yl)amino]pyrimidine-5-carboxylate (64 mg) was dissolved in ethanol (3 ml), and the solution was added with a 20% aqueous solution of KOH (0.5 ml) and heated at reflux. After the disappearance of the materials was observed with TLC, the reaction mixture was poured into 2 N hydrochloric acid, and extracted with ethyl acetate. The organic layer was, dried over $Na_2SO_4$, and the solvent was evaporated to give white crude crystals of compound 6 (57 mg, 96%).

Compound 6:
Colorless Needles (EtOH); mp>300° C.
$^1$HNMR (400 MHz, DMSO-$d_8$) δ 8.83 (br s, 1 H), 8.68 (br s, 1 H), 7.22 (s, 1 H), 7.14 (s, 1 H), 3.41 (s, 3 H), 1.96 (s, 3 H), 1.65 (s, 4 H), 1.28 (s, 3 H), 1.26 (s, 3 H), 1.22 (B, 3 H), 1.20 (s, 3 H).;
Anal. Calcd for $C_{21}H_{27}N_3O_2$, C: 71.36%, H: 7.70%, N: 11.89%; Found C: 71.26%, H: 7.74%, N: 11.77%.

Example 7

Preparation of 2-[N-n-Propyl-N-(5,6,7,8-tetrahydro-3,5,5,8,8-pentamethyl-naphthalen-2-yl)amino]pyrimidine-5-carboxylic Acid (Compound 7)

Ethyl 2-[N-(5,6,7,8-tetrahydro-3,5,5,8,8-pentamethylnaphthalene-2-yl)amino]-pyrimidine-5-carboxylate (60 mg) was dissolved in dry DMF (2 ml), and the solution was added with a suspension of NaH (50 mg) in DMF (2 ml) and stirred. Then, the mixture was added with n-propyl iodide (0.5 ml) and stirred. After the disappearance of the materials was observed with TLC, the reaction mixture was poured into water, and extracted with $CH_2Cl_2$. The organic layer was dried over $Na_2SO_4$, and the solvent was evaporated. The residue was purified by silica gel flash column chromatography (n-hexane: AcOEt=20:1) to obtain a mixture of ethyl 2-[N-n-propyl-N-(5,6,7,8-tetrahydro-3,5,5,8,8-pentamethylnaphthalen-2-yl)amino]pyrimidine-5-carboxylate and its n-propyl ester derivative (72 mg).

$^1$H-NMR (400 MHz, CDCl$_3$) δ 8.94 (s, 1 H), 8.78 (s, 1 H), 7.18 (s, 1 H), 7.0 (s, 1 H), 4.33 (q, J=7.2 Hz, 2 H), 4.02 (m, 1 H), 3.61 (m, 1 H), 2.05 (s, 3 H), 1.73 (6 th, J=7.3 Hz, 2 H), 1.69 (s, 4 H), 1.32 (t, J=7.3 Hz, 3 H), 1.32 (s, 3 H), 1.28 (a, 3 H), 1.26 (s, 3 H), 1.25 (s, 3 H), 0.93 (t, J=7.3 Hz, 3H).

Ethyl 2-[N-n-propyl-N-(5,6,7,8-tetrahydro-3,5,5,8,8-pentamethylnaphthalen-2-yl)amino]pyrimidine-5-carboxylate (72 mg) was dissolved in ethanol (3 ml), and the solution was added with a 20% aqueous solution of KOH (0.5 ml) and heated at reflux. After the disappearance of the materials was observed with TLC, the reaction mixture was poured into 2 N hydrochloric acid, and extracted with ethyl acetate. The organic layer was dried over $Na_2SO_4$, and the solvent was evaporated to give white crude crystals of compound 7 (66 mg, quant).

Compound 7:

Colorless Needles (n-hexane-AcOEt); mp 193° C.;

$^1$H-NMR (400 MHz, CDCl$_3$) δ 9.01 (s, 1 H), 8.84 (s, 1 H), 7.21 (a, 1 H), 7.0 (s, 1 H), 4.09 (m, 1 H), 3.64 (m, 1 H), 2.07 (s, 3 H), 1.71 (6 th, J=7.3 Hz, 2 H), 1.69 (s, 4 H), 1.33 (s, 3 H), 1.28 (s, 3 H), 1.26 (s, 6 H), 0.95 (t, J=7.3 Hz, 3 H);

Example 8

Preparation of 2-[N-Cyclopropylmethyl-N-(5,6,7,8-tetrahydro-3,5,5,8,8-pentamethylnaphthalen-2-yl)amino]pyrimidine-5-carboxylic Acid (Compound 8)

Ethyl 2-[N-(5,6,7,8-tetrahydro-3,5,5,8,8-pentamethylnaphthalene-2-yl)amino]-pyrimidine-5-carboxylate (80 mg) was dissolved in dry DMF (2 ml), and the solution was added with a suspension of NaH (45 mg) in DMF (2 ml). The mixture was added with cyclopropylmethyl bromide (0.3 ml) and stirred at 50° C. After the disappearance of the materials was observed with TLC, the reaction mixture was poured into water, and extracted with CH$_2$Cl$_2$. The organic layer was dried over Na$_2$SO$_4$, and the solvent was evaporated. The residue was purified by silica gel flash column chromatography (CH$_2$Cl$_2$) to obtain a mixture of ethyl 2-[N-cyclopropylmethyl-N-(5,6,7,8-tetrahydro-3,5,5,8,8-pentamethylnaphthalene-2-yl)amino]pyrimidine-5-carboxylate and its n-cyclopropyl methyl ester (69 mg).

Ethyl 2-[N-cyclopropylmethyl-N5,6,7,8-tetrahydro-3,5,5,8,8-pentamethyl-naphthalen-2-yl)amino]pyrimidine-5-carboxylate (69 mg) was dissolved in ethanol (3 ml), and the solution was added with a 20% aqueous solution of KOH (0.5 ml) and heated at reflux. After the disappearance of the materials was observed with TLC, the reaction mixture was poured into 2 N hydrochloric acid, and extracted with ethyl acetate. The organic layer was dried over Na$_2$SO$_4$, and the solvent was evaporated to give white crude crystals of compound 8 (59 mg, 69%).

Compound 8:

Pale Yellow Prisms (CH$_3$OH); mp 123° C.;

$^1$H-NMR (400 MHz, CDCl$_3$) δ 8.96 (s, 1 H), 8.83 (B, 1 H), 7.18 (s, 1 H), 7.11 (a, 1 H), 4.10 (dd, J=6.6, 14.1 Hz, 1 H), 3.47 (d, J=7.5 Hz, 1 H), 2.08 (s, 3 H), 1.69 (br s, 2 H), 1.68 (br a, 2 H), 1.33 (s, 3 H), 1.27 (s, 3 H), 1.26 (s, 6 H), 1.19 (br m, 1 H), 0.47 (br m, 2 H), 0.22 (br m, 2 H);

Anal. Calcd for C$_{24}$H$_{31}$N$_3$O$_2$.¼H$_2$O, C: 72.42%, H: 7.98%, N: 10.56%; Found C: 72.46%, H: 7.94%, N: 10.35%.

Example 9

Preparation of 2-[N-(3,5-Di-tert-butylphenyl)-N-methylamino] pyrimidine-5-carboxylic Acid (Compound 9)

A mixture of ethyl 2-chloropyrimidine-5-carboxylate (335 mg), 3,5-di-tert-butylaniline (370 mg), and K$_2$CO$_3$ (600 mg) was heated at 110° C. After the disappearance of the materials was observed with TLC, the reaction mixture was poured into water, and extracted with CH$_2$Cl$_2$. The organic layer was dried over Na$_2$SO$_4$, and the solvent was evaporated. The residue was purified by silica gel flash column chromatography (n-hexane: AcOEt=10:1) to give white crystals of ethyl 2-[N-(3,5-di-tert-butylphenyl)amino] pyrimidine-5-carboxylate (574 mg, 90%).

$^1$H-NMR (400 MHz, CDCl$_3$) δ 8.96 (s, 2 H), 7.47 (d, J=1.7 Hz, 2 H), 7.41 (s, 1 H), 7.21 (t, J=1.7 Hz, 1 H), 4.37 (q, J=7.1 Hz, 2 H), 1.40 (t, J=7.1 Hz, 3 H), 1.35 (s, 18 H).

Ethyl 2-(N-(3,5-di-tert-butylphenyl)aminopyrimidine-5-carboxylate (50 mg) was dissolved in dry DMF (2 ml), and the solution was added with a suspension of NaH (45 mg) in DMF (1 ml). The mixture was then added with methyl iodide (0.3 ml) and stirred. After the disappearance of the materials was observed with TLC, the reaction mixture was poured into water, and extracted with CH$_2$Cl$_2$. The organic layer was dried over Na$_2$SO$_4$, and the solvent was evaporated. The residue was purified by silica gel flash column chromatography (n-hexane: AcOEt=20:1) to obtain white crystals of ethyl 2-[N-(3,5-di-tert-butylphenyl)-N-methylamino]-pyrimidine-5-carboxylate (49 mg, 95%).

$^1$H-NMR (CDCl$_3$) 8.86 (s, 2 H), 7.35 (t, J=1.8 Hz, 1 H), 7.12 (d, J=1.8 Hz, 2 H), 4.34 (q, J=7.1 Hz, 2 H), 3.69 (s, 3 H), 1.35 (t, J=7.1 Hz, 3 H), 1.34 (s, 18 H).

Ethyl 2-[N3,5-di-tert-butylphenyl)-N-methylamino] pyrimidine-5-carboxylate (49 mg) was dissolved in ethanol (4 ml), and the solution was added with a 20% aqueous solution of KOH (1 ml) and heated at reflux. After the disappearance of the materials was observed with TLC, the reaction mixture was poured into 2 N hydrochloric acid, and extracted with ethyl acetate. The organic layer was dried over Na$_2$SO$_4$, and the solvent was evaporated to give white crude crystals of compound 9 (47 mg, quant).

Compound 9:

Colorless Needles (n-hexane-AcOEt); mp 261–263° C.;

$^1$H-NMR (400 MHz, DMSO-d$_6$) δ 8.74 (s, 2 H), 7.31 (br s, 1 H), 7.14 (br s, 2 H), 3.51 (s, 3 H), 1.29 (s, 18 H);

Anal. Calcd for C$_{20}$H$_{27}$N$_3$O$_2$.⅓H$_2$O, C: 69.13%, H: 8.03%, N: 12.10%; Found C: 69.19%, H: 7.78%, N: 11.87%.

Example 10

Preparation of 2-[N-Ethyl-N-(3,5-di-tert-butylphenyl)amino]pyrimidine-5-carboxylic Acid (Compound 10)

Ethyl 2-[N-(3,5-di-tert-butylphenyl)amino]pyrimidine-5-carboxylate (50 mg) was dissolved in dry DMF (2 ml), and the solution was added with a suspension of NaH (45 mg) in DMF (1 ml). The mixture was then added with ethyl iodide (0.3 ml) and stirred. After the disappearance of the materials was observed with TLC, the reaction mixture was poured into water, and extracted with CH$_2$Cl$_2$. The organic layer was dried over Na$_2$SO$_4$, and the solvent was evaporated. The residue was purified by silica gel flash column chromatography (n-hexane: AcOEt=10:1) to obtain white crystals of ethyl 2-[N-ethyl-N-(3,5-di-tert-butylphenyl)amino] pyrimidine-5-carboxylate (53 mg, 99%).

$^1$H-NMR (400 MHz, CDCl$_3$) δ 8.84 (s, 2H), 7.37 (t, J=1.7 Hz, 1 H), 7.06 (d, J=1.8 Hz, 2 H), 4.33 (q, J=7.1 Hz, 2 H), 4.05 (q, J=7.2 Hz, 2 H), 1.35 (t, J=7.1 Hz, 3 H), 1.34 (s, 18 H), 1.26 (t, J=7.1 Hz, 3 H).

Ethyl 2-[N-ethyl-N-(3,5-di-tert-butylphenyl)amino] pyrimidine-5-carboxylate (53 mg) was dissolved in ethanol (4 ml), and the solution was added with a 20% aqueous solution of KOH (1 ml) and heated at reflux. After the disappearance of the materials was observed with TLC, the reaction mixture was poured into 2 N hydrochloric acid, and extracted with ethyl acetate. The organic layer was dried over Na$_2$SO$_4$, and the solvent was evaporated to give white crude crystals of compound 10 (49 mg, 99%).

Compound 10:

Colorless Cottons (n-hexane-AcOEt); mp 277° C.;

$^1$H-NMR (400 MHz, DMSO-d$_6$) δ 8.73 (s, 2 H), 7.34 (br s, 1 H), 7.06 (br s, 2 H), 3.99 (q, J=7.0 Hz, 2 H), 1.29 (s, 18 H), 1.17 (t, J=7.0 Hz, 3 H);

Anal. Calcd for C$_{21}$H$_{29}$N$_3$O$_2$.⅙H$_2$O, C: 70.35%, H: 8.25%, N: 11.72%; Found C: 70.37%, H: 8.06%, N: 11.64%.

Example 11

Preparation of 2-[N-(3,6-Di-tert-butylphenyl)-N-n-propylamino]pyrimidine-5-carboxylic Acid (Compound 11)

Ethyl 2-[N-(3,5-di-tert-butylphenyl)amino]pyrimidine-5-carboxylate (50 mg) was dissolved in dry DMF (2 ml), and the solution was added with a suspension of NaH (40 mg) in DMF (1 ml). The mixture was then added with n-propyl iodide (0.3 ml) and stirred. After the disappearance of the materials was observed with TLC, the reaction mixture was poured into water, and extracted with $CH_2Cl_2$. The organic layer was dried over $Na_2SO_4$, and the solvent was evaporated. The residue was purified by silica gel flash column chromatography (n-hexane: AcOEt=10:1) to obtain a mixture of ethyl 2-[N-(3,5-di-tert-butylphenyl)-N-n-propylamino]-pyrimidine-5-carboxylate and its n-propyl ester derivative (56 mg).

Ethyl 2-[N3,5-di-tert-butylphenyl)-N-n-propylamino]pyrimidine-5-carboxylate (56 mg) was dissolved in ethanol (4 ml), and the solution was added with a 20% aqueous solution of KOH (1 ml) and heated at reflux. After the disappearance of the materials was observed with TLC, the reaction mixture was poured into 2 N hydrochloric acid, and extracted with ethyl acetate. The organic layer was dried over $Na_2SO_4$, and the solvent was evaporated to give white crude crystals of compound 11 (51.5 mg, 99%).

Compound 11:
Colorless Prisms (n-hexane-$CH_2Cl_2$); mp 219° C.;
$^1$H-NMR (400 MHz, $CDCl_3$) δ 8.87 (s, 2 H), 7.39 (t, J=1.8 Hz, 1 H), 7.06 (d, J=1.7 Hz, 2 H), 3.96 (m, 2H), 1.71 (6th, J=7.5 Hz, 2 H), 1.34 (s, 18 H), 0.94 (t, J=7.4 Hz, 3 H);
Anal. Calcd for $C_{22}H_{31}N_3O_2 \cdot \frac{1}{3}H_2O$, C: 70.82%, H: 8.48%, N: 11.27%; Found C: 70.79%, H: 8.27%, N: 11.18%.

Example 12

Preparation of 2-[N-Cyclopropylmethyl-N-(3,5-di-tert-butylphenyl)-amino]pyrimidine5-carboxylic Acid (Compound 12)

Ethyl 2-[N-(3,5-di-tert-butylphenyl)amino]pyrimidine5-carboxylate (50 mg) was dissolved in dry DMF (2 ml), and the solution was added with a suspension of NaH (45 mg) in DMF (1 ml). The mixture was then added with cyclopropylmethyl bromide (0.2 ml) and stirred. After the disappearance of the materials was observed with TLC, the reaction mixture was poured into water, and extracted with $CH_2Cl_2$. The organic layer was dried over $Na_2SO_4$, and the solvent was evaporated. The residue was purified by silica gel flash column chromatography (n-hexane: AcOEt=10:1) to obtain a mixture of ethyl 2[N-cyclopropylmethyl-N-(3,5-di-tert-butylphenyl)amino]pyrimidine-5-carboxylate and its cyclopropylmethyl ester derivative (55 mg, 96%).

$^1$H-NMR (400 MHz, $CDCl_3$) δ 8.84 (9, 2 H), 7.37 (t, J=1.7 Hz, 1 H), 7.10 (d, J=1.7 Hz, 2 H), 4.33 (q, J=7.1 Hz, 2H), 3.87 (d, J=6.8 Hz, 2 H), 1.35 (t, J=7.2 Hz, 3 H), 1.34 (s, 18 H), 1.26 (br m, 1 H), 0.46 (m, 2 H), 0.18 (d, J=4.6 Hz, 10.5 Hz, 2 H).

Ethyl 2-[N-cyclopropylmethyl-N-(3,5-di-tert-butylphenyl)amino]pyrimidine-5-carboxylate (55 mg) was dissolved in ethanol (4 ml), and the solution was added with a 20% aqueous solution of KOH (1 ml) and heated at reflux. After the disappearance of the materials was observed with TLC, the reaction mixture was poured into 2 N hydrochloric acid, and extracted with ethyl acetate. The organic layer was dried over $Na_2SO_4$, and the solvent was evaporated to give compound 12 (51.5 mg, quant).

Compound 12:
Colorless Powder (n-hexane-$CH_2Cl_2$); mp 194° C.;
$^1$H-NMR (400 MHz, $CDCl_3$) δ 8.89(s, 2 H), 7.40 (t, J=1.8 Hz, 1 H), 7.11 (d, J=1.8 Hz, 2 H), 3.89 (d, J=7.0 Hz, 2 H), 1.34 (s, 18 H), 1.18 (br m, 1 H), 0.48 (dd, J=4.6, 13 Hz, 2 H), 0.20 (dd, J=5, 10.1 Hz, 2 H);
Anal. Calcd for $C_{23}H_{31}N_3O_2 \cdot \frac{1}{3}H_2O$, C: 71.28%, H: 8.24%, N: 10.85%; Found C: 71.29%, H: 7.99%, N: 10.73%.

Test Example 1

Cell Differentiation-Inducing Activity Test in HL-60 Cell

By using the above compounds, cell differentiation-inducing activity of each compound alone, and effect on cell differentiation-inducing action of a co-existing retinoid were examined. As a comparative and co-existing retinoid, Am80: 4-[(5,6,7,8-tetrahydro-5,5,8,8-tetramethyl-2-naphthalenyl)carbamoyl]benzoic acid ($1 \times 10^{-10}$ M) was used. According to the method described in Japanese Patent Unexamined Publication (KOKAI) No.(Sho)61-76440/1986, promyelocytic leukemia cell stain HL-60 was used, and differentiation into granulocytic cells was determined by observing morphological change and measuring ability to reduce nitroblue tetrazolium (NBT). The ratios of differentiated cells shown in the following table were calculated from the ability of reducing NBT. The results are shown on Table 1.

TABLE 1

| Compound No. | Ratio of differentiated cells by each compound alone (%) Concentration (M) | | | Ratio of differentiated cells by each compound co-existing with $1 \times 10^{-10}$ M Am80 (%) Concentration (M) | | | | |
|---|---|---|---|---|---|---|---|---|
| | $10^{-8}$ | $10^{-7}$ | $10^{-6}$ | none | $10^{-11}$ | $10^{-10}$ | $10^{-9}$ | $10^{-8}$ | $10^{-7}$ |
| 1 | 2 | 2 | 44 | 10 | 19 | 17 | 22 | 17 | 39 |
| 2 | 2 | 37 | 81 | 5 | 6 | 7 | 18 | 81 | 78 |
| 3 | 9 | 14 | 16 | 11 | 27 | 60 | 90 | 87 | 89 |
| 4 | 6 | 9 | 6 | 10 | 43 | 71 | 74 | 83 | 89 |
| 5 | 1 | 3 | 9 | 10 | 18 | 18 | 25 | 49 | 85 |
| 6 | 2 | 11 | 10 | 5 | 5 | 16 | 58 | 81 | 78 |
| 7 | 2 | 3 | 2 | 10 | 23 | 53 | 76 | 83 | 82 |
| 8 | 3 | 4 | 4 | 5 | 9 | 26 | 63 | 84 | 81 |
| 9 | 2 | 1 | 1 | 2 | 12 | 17 | 14 | 18 | 24 |
| 10 | 1 | 3 | 2 | 2 | 18 | 15 | 18 | 38 | 81 |
| 11 | 1 | 2 | 1 | 2 | 18 | 29 | 47 | 87 | 86 |
| 12 | 2 | 3 | 3 | 2 | 19 | 27 | 59 | 80 | 90 |

What is claimed is:

1. A compound or a salt thereof represented by the following formula (I):

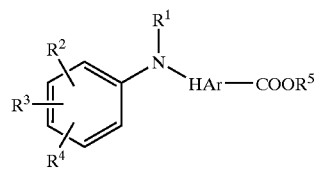

wherein $R^1$ represents hydrogen atom, a $C_{1-6}$ alkyl group, a $C_{1-6}$ alkenyl group, or an acyl group, $R^2$ and $R^3$ independently represent hydrogen atom or a $C_{1-6}$ alkyl group or adjacent $R^2$ and $R^3$ may combine together with carbon atoms on the benzene ring to which they bind to form an aromatic 5- to 7-membered ring or non-aromatic 5- to 7-membered ring which may be substituted; $R^4$ represents hydrogen atom, hydroxyl group, a $C_{1-6}$ alkoxyl group, a $C_{1-6}$ alkyl group, nitro group, or a halogen atom; and HAr—COOR$^5$ is 5-carboxy-pyrimidine-2-yl.

2. A medicament composition which comprises the compound according to claim 1 or a physiologically acceptable salt thereof as an active ingredient.

3. A method for therapeutic treatment of diabetes comprising administering to a patient a therapeutically effective amount of the compound of claim 1 or a physiologically acceptable salt thereof.

4. A method for preventive treatment of diabetes comprising administering to a patient a preventively effective amount of the compound of claim 1 or a physiologically acceptable salt thereof.

5. A method for therapeutic treatment of complications of diabetes comprising administering to a patient a therapeutically effective amount of the compound of claim 1 or a physiologically acceptable salt thereof.

6. The method according to claim 5 wherein the complications of diabetes include at least one of retinopathy, nephrosis, neuropathy and hyperlipidemia.

7. A method for preventive treatment of complications of diabetes comprising administering to a patient a preventively effective amount of the compound of claim 1 or a physiologically acceptable salt thereof.

8. The method according to claim 7 wherein the complications of diabetes include at least one of retinopathy, nephrosis, neuropathy and hyperlipidemia.

9. A method for controlling retinoid action comprising administering to a patient the compound of claim 1 or a physiologically acceptable salt thereof to control retinoid action.

* * * * *

UNITED STATES PATENT AND TRADEMARK OFFICE
CERTIFICATE OF CORRECTION

PATENT NO. : 6,869,959 B1
DATED : March 22, 2005
INVENTOR(S) : H. Kagechika

It is certified that error appears in the above-identified patent and that said Letters Patent is hereby corrected as shown below:

<u>Title page,</u>
Item [56], References Cited, FOREIGN PATENT DOCUMENTS, "EP 493528" should be -- CH 493528 -- "EP 2926644" should read -- DE 2926644 --.

Signed and Sealed this

First Day of November, 2005

JON W. DUDAS
*Director of the United States Patent and Trademark Office*